United States Patent [19]  [11] Patent Number: 4,541,437
Amemiya  [45] Date of Patent: Sep. 17, 1985

[54] ULTRASONIC PULSE DOPPLER BLOOD FLOW METER

[75] Inventor: Shin-ichi Amemiya, Yokohama, Japan

[73] Assignee: Fujitsu Limited, Kawasaki, Japan

[21] Appl. No.: 516,554

[22] Filed: Jul. 25, 1983

[30] Foreign Application Priority Data

Jul. 28, 1982 [JP] Japan .................. 57-131602

[51] Int. Cl.⁴ .......................... A61B 101/00
[52] U.S. Cl. .................... 128/663; 73/861.25
[58] Field of Search ............ 128/663; 73/861.25

[56] References Cited

U.S. PATENT DOCUMENTS

| | | | |
|---|---|---|---|
| 4,060,763 | 12/1977 | Hassler | 128/660 |
| 4,122,713 | 10/1978 | Stasz et al. | 128/663 |
| 4,143,650 | 3/1979 | Hathe | 128/660 |
| 4,227,407 | 10/1980 | Drost | 128/663 X |
| 4,357,278 | 3/1981 | Papadofrongakis et al. | 128/663 X |
| 4,357,944 | 11/1982 | Mauser et al. | 128/663 |
| 4,391,148 | 7/1983 | Sainz et al. | 128/663 X |
| 4,434,669 | 3/1984 | Roberts et al. | 128/663 X |

FOREIGN PATENT DOCUMENTS 351146 10/1979 German Democratic Rep. ................ 128/660

OTHER PUBLICATIONS

Mauser, R., "Cardiotachometer", Eüropäische Patent on Melding 0 027215, published Oct. 1980.

Primary Examiner—Kyle L. Howell
Assistant Examiner—Francis J. Jaworski
Attorney, Agent, or Firm—Staas & Halsey

[57] ABSTRACT

An ultrasonic pulse Doppler blood flow meter, wherein an amplitude equalizing circuit is inserted between the high-pass filter provided in the successive stage of the Doppler detector and the Doppler analyzer. The amplitude equalizing circuit not only effectively utilizes the input dynamic range of the Doppler analyzer but also automatically adjusts the cut-off frequency of the high-pass filter in accordance with the input signal. Therefore, a blood flow meter which requires minimal manual adjustment is obtained.

8 Claims, 7 Drawing Figures

ULTRASONIC PULSE DOPPLER BLOOD FLOW METER

BACKGROUND OF THE INVENTION (1) Field of the Invention

This invention relates to an ultrasonic pulse Doppler blood flow meter, and more specifically to the characteristic control of a receiving circuit.

(2) Description of the Prior Art

An ultrasonic pulse Doppler blood flow meter, which measures a blood flow rate and its distribution by transmitting an ultrasonic pulse wave to living body tissue and by receiving a reflected wave from a blood corpuscle, is currently attracting attention. The equipment currently being used requires many manual adjustments and is not easy to operate.

FIG. 1 is a block diagram of a conventional ultrasonic pulse Doppler blood flow meter. In FIG. 1, 1 is a master oscillator, 2 is a transmitting timing generator which generates a transmitting timing signal by dividing an output of the master oscillator, 3 is a transmitting amplifier which generates a pulse or burst transmitting signal, 4 is a transducer (ultrasonic wave probe) which generates an ultrasonic wave to a living body in accordance with the transmitting signal and receives a reflected wave from the living body, 5 is a receiving amplifier which amplifies the reflected wave signal received by the transducer and 6 and 7 are real (R) and imaginary (I) Doppler element detectors. The detectors 6 and 7 include mixers 61 and 71 which receive the cosine and sine signals, allow a phase difference of 90° from the master oscillator and carry out orthogonal detection, low-pass filters (LPFs) 62 and 72 and sample and hold circuits (S/H) 63 and 73. The detector 6 detects a real element of the Doppler signal reflected from the specified depth (distance between the probe and the location generating the reflected wave), while the detector 7 detects the imaginary element of the Doppler signal. High-pass filters 8 and 9 (HPFs) eliminate a low frequency Doppler element, generated by the wall of the heart, at the outputs of the detectors 6 and 7. A Doppler analyzer 10 is provided with an A/D converter and a digital processor which analyzes frequency by a fast Fourier transformation (FFT) at the outputs of the filters 8 and 9 (the Doppler element indicating a blood flow rate). A display 11 is used for indicating the result of the analysis. A sample pulse generator 12 generates the sample pulse to the sample hold circuits 63 and 73 in accordance with a position designation signal and the output of the transmitting timing generator 2. As explained above, since the cosine and sine reference signals, allowing a phase difference of 90°, are input to the mixers 61 and 71 from the master oscillator and orthogonal detection is carried out by the detectors 6 and 7. A gain of the receiving amplifier 5 can be adjusted by a variable resistor 13 provided at the operation panel for gain control.

In the Doppler blood flow meter of this type, since the HPFs 8 and 9 have an upper limit input level (about ±10 V), an output level of the HPF becomes low when the Doppler signal contains a low frequency element due to movement of the wall of the heart and, therefore, the Doppler analyzer 10 in the next stage must be highly accurate. However, there are other problems: (1) brightness of the display 11 must be adjusted; (2) a cut-off frequency of the HPFs 8 and 9 must be changed in accordance with a blood flow rate; and (3) a gain of the receiving amplifier must also be changed in accordance with the level of the receiving signal.

SUMMARY OF THE INVENTION

It is an object of the present invention to alleviate the above-mentioned problems such as manual adjustment of the amplifier gain and selection of the cut-off frequency of the filters. The present invention causes the successive circuits of the receiving amplifier to operate efficiently. The Doppler analyzer performs an accurate analysis by employing an AGC type receiving amplifier 5 after an HPF (high pass filter) for adding the amplitude of a signal from an equalizing circuit located in a successive stage of the HPFs. AGC type amplifiers are used before and after a Doppler detector to improve the accuracy of the device.

The ultrasonic pulse Doppler blood flow meter of this invention includes an ultrasonic probe which transmits and receives ultrasonic waves to living body tissue at a specified repetition frequency, a receiving amplifier which amplifies reflected ultrasonic wave signals obtained from the ultrasonic probe, a Doppler detector which mixes an output of the receiving amplifier and the reference signal and generates a Doppler signal of the specified depth, a high pass filter which eliminates a low frequency element of the Doppler signal, an amplitude equalizing circuit which equalizes the amplitude of an output of the high pass filter, a Doppler analyzer which analyzes an output of the amplitude equalizing circuit, and a display which displays the results of the analysis of the Doppler analyzer.

The present invention will be explained in detail by way of the preferred embodiment of the invention with reference to the drawings.

DESCRIPTION OF THE PREFERRED EMBODIMENT

Figure 1:
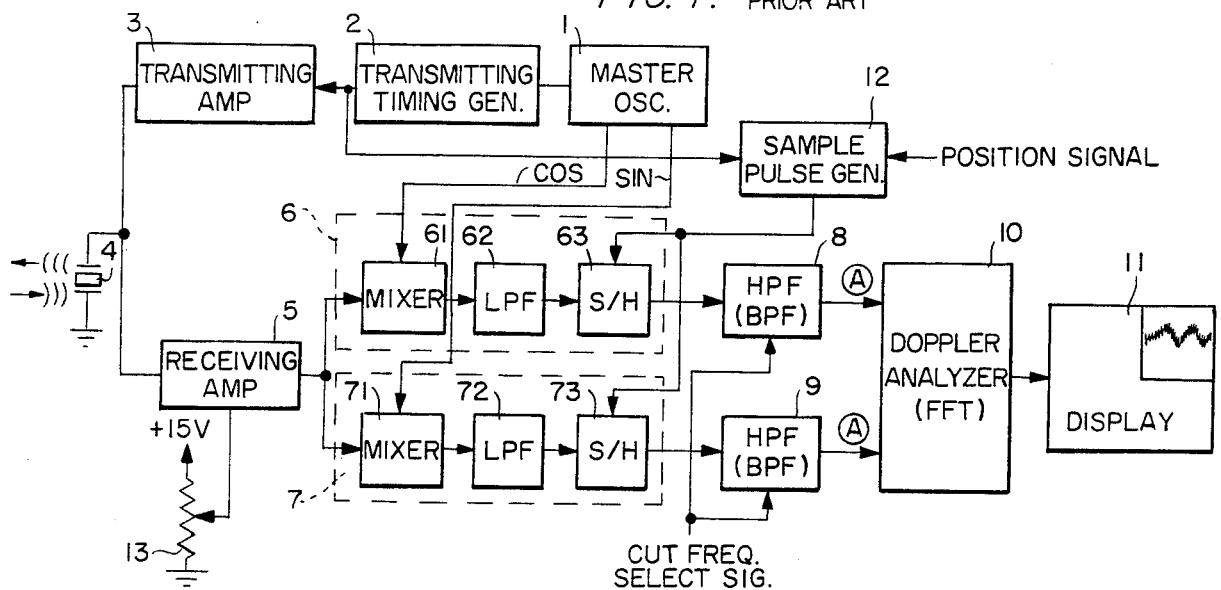
FIG. 1 is a block diagram of a conventional ultrasonic pulse Doppler blood flow meter.
Figure 2:
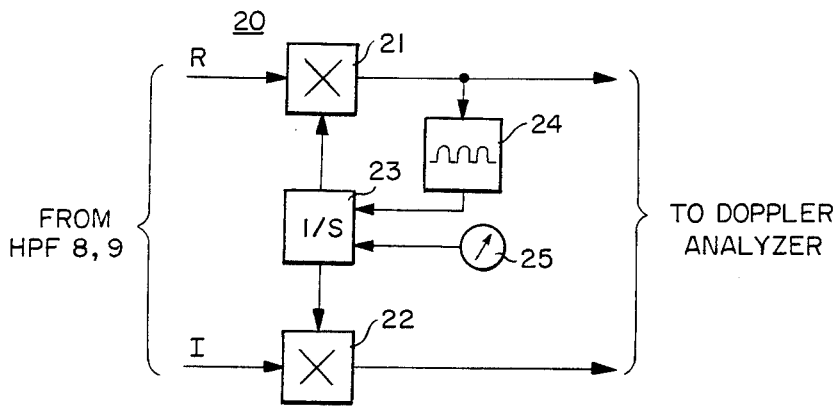
FIG. 2 is a block diagram of an amplitude equalizing circuit in accordance with an embodiment of the present invention.

FIG. 2 is a block diagram of the amplitude equalizing circuit 20 to be inserted into the A — A part of FIG. 1, in accordance with an embodiment of the present invention. A multiplier 21 receives the output R from the HPF 8 as an input and a multiplier 22 receives the output I from the HPF 9 as an input. An integral circuit 23 multiplies the output amplitudes of the HPFs 8 and 9. A full-wave or half-wave detector 24 detects the output amplitude of the HPF 8. A level setter 25 designates the desired signal level and a difference between the outputs of the detector 24 and the level setter 25 is integrated by the integrator circuit 23. The result is input as the gain control signal to the multiplier 21 which is a variable gain amplifier. Therefore, an average value $\sqrt{R^2+I^2}$ of the signals R and I applied to the Doppler analyzer 10 is constant (for example, 5 Vp−p). In this embodiment, only the output of the multiplier 21 is detected because the amplitude of the signals R and I are almost equal.

Figure 3:
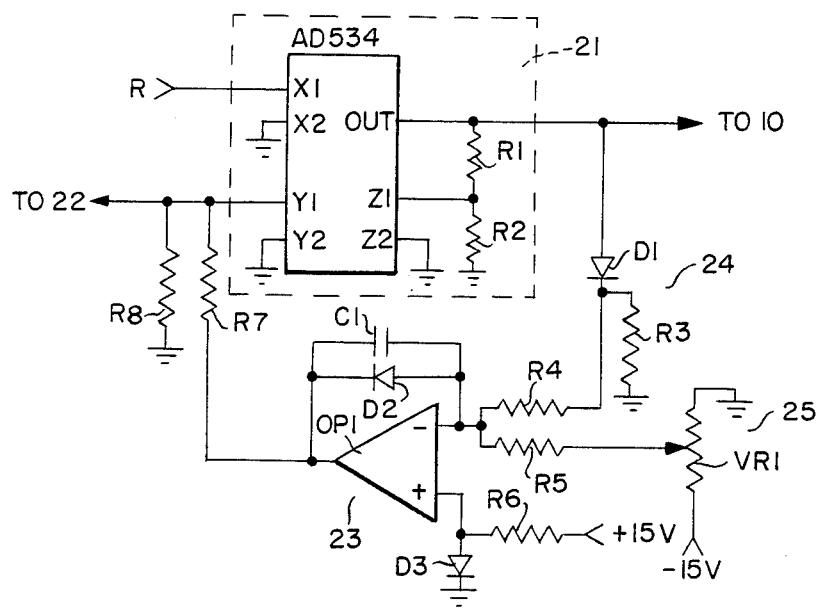
FIG. 3 is a detailed diagram of FIG. 2.

FIG. 3 is a detailed circuit diagram of FIG. 2. The multiplier 21 comprises an integrated circuit chip AD 534 and resistors $R_1$ and $R_2$. The multiplier 22 also has the same structure but is omitted in the figure. A diode $D_1$ and resistor $R_3$ form a half-wave detector 24. The resistors $R_4$ and $R_5$ and the level setting variable resistor $VR_1$ form an adder circuit and the difference thereof is input to the integral circuit 23. The integrator circuit 23 comprises an operational amplifier $OP_1$, resistors $R_6$ and $R_8$, diodes $D_2$ and $D_3$ and a capacitor $C_1$. Of these elements, a feedback gain and level adjusting response rate are determined by a time constant circuit $C_1R_4$. An adequate time constant is a single Doppler analysis time (about 30 msec). The diode $D_2$ prevents an output of the operational amplifier $OP_1$ from becoming negative. The diode $D_3$ is connected to the positive (reference) input side of the operational amplifier OP in order to compensate for a voltage gap of about 0.7 V by the diode $D_2$. The resistors $R_7$ and $R_8$ divide the maximum output value of the operational amplifier OP (about 12 V when the power source of +15 V is used) into a value suitable for the input of the multiplier 21. For example, when an input limit of the integrated circuit chip AD 534 is 10 V, it is divided into 10/12 by the resistors $R_7$ and $R_8$. The resistors $R_1$ and $R_2$ of multiplier 21 are used for setting the maximum amplification degree expressed by the following relationship in the case of the integrated circuit AD 534. The maximum amplification degree is equal to:

$(R_1+R_2)/R_2$

Figure 4:
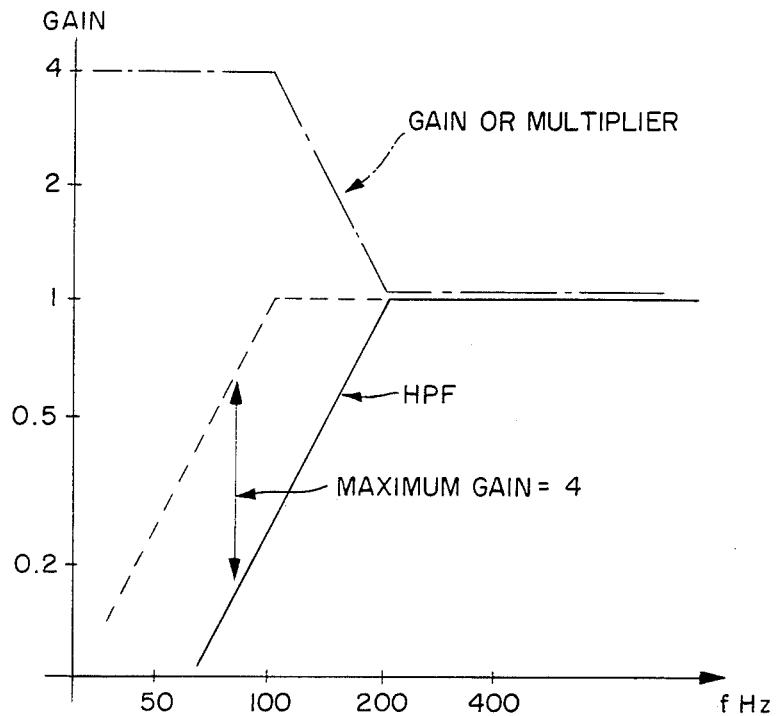
FIG. 4 is a graph of the frequency characteristic of the amplitude equalizing circuit of FIG. 2.

The following two advantages can be obtained by inserting the above-mentioned amplitude equalizing circuit 20 between A — A. First, since an input amplitude of the Doppler analyzer is fixed even if the gain control of the HPFs 8 and 9 is insufficient, the dynamic range of the A/D converter at the input stage of the analyzer or digital processor in the successive stage can be used sufficiently. Thereby, adjustment of the brightness of the display 11 is no longer necessary. Second, since a cut-off of the filter frequency changes automatically, it is no longer necessary to adjust the cut-off frequency selection signal. FIG. 4 is a graph of the frequency characteristics for explaining these advantages. A transfer characteristic for the inputs of ±10 V of the HPFs 8 and 9 is indicated by a solid line, and a transfer characteristic of the amplitude equalizing circuit 20 is indicated by a broken line. When an input signal is 200 Hz or less, the output level drops and, accordingly, the gain of the amplitude equalizing circuit increases as indicated by the broken line and becomes constant at the maximum value. Therefore, the overall frequency characteristic spreads to a lower frequency region as indicated by the broken line. In this case, a single frequency is used. When high frequency components generated by blood flow and low frequency components generated by the wall of the heart co-exist, the frequency characteristic is as follows. When the blood flow rate is high and the frequency is 400 Hz in terms of the Doppler frequency, an output level of HPF is high, the amplitude equalizing circuit does not operate to increase the amplitude, a frequency component of about 100 Hz generated by the wall of the heart is effectively suppressed and, therefore, the overall characteristic is shown by the solid line in FIG. 4. On the other hand, when the blood flow rate is low and has a frequency of about 100 Hz, movement of the wall of the heart is also low and the Doppler frequency can become as low as 30 Hz. At any rate, since the Doppler frequency becomes lower than the cut-off frequency of the HPF, an output level of the HPF is low and, therefore, the amplitude equalizing circuit starts operating and, accordingly, the overall characteristic, as shown by the broken line, is obtained. That is, a sufficient gain is obtained for the frequency of 100 Hz of the blood flow, but almost no gain is obtained for the 30 Hz frequency of the wall of the heart. In this case, the blood flow component and heart wall component, that is, the signal and noise, can be isolated. According to this circuit, a cut-off frequency of the filter is automatically lowered when the blood flow rate is low, and automatically increases when the blood flow rate is high and thereby the low frequency component of the heart can be eliminated. If the characteristic of the HPF is not different from the above case when the blood flow rate is low, only noise is obtained. In the case of conventional methods, this phenomenon can be prevented by manual adjustment of the cut-off frequency fc of the HPF. However, according to this invention, the frequency adjustment is executed automatically and the dynamic range of successive stages, that is, the Doppler analyzer can eliminate the low frequency component of the heart and still pick up a low blood flow rate.

When there is no distortion in the circuits up to the input of the Doppler detectors 6 and 7, a high precision Doppler analysis is carried out with the maximum effect of the amplitude equalizing circuit 20 as explained above. Since the output level of the transducer fluctuates greatly, gain control of the receiving amplifier 5 is necessary in order to eliminate any distortion. If the gain control is adjusted manually, as in the case of FIG. 1, the operations are very complicated and the effect obtained is also insufficient.

Figure 5:
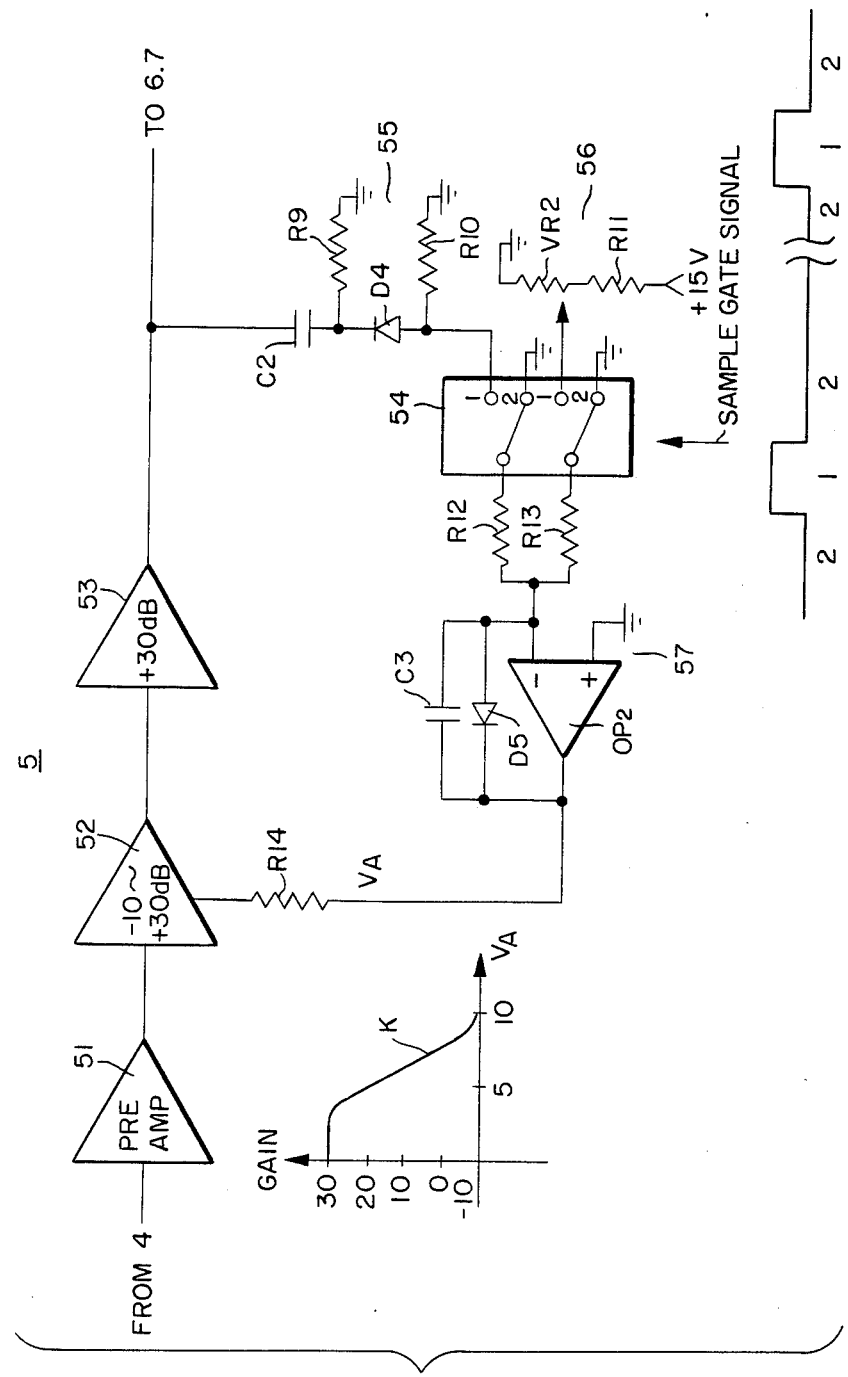
FIG. 5 is a schematic diagram of an automatic gain control type receiving amplifier.

FIG. 5 is a circuit diagram of the receiving amplifier 5. The receiving amplifier 5 has a series connection of a preamplifier 51 which amplifies a receiving signal, an AGC amplifier 52 having an approximate gain of from −10 dB to +30 dB and an amplifier 53 having a gain of +30 dB. The feedback path of the AGC amplifier 52 is provided with a detector for half-wave rectification comprising a diode $D_4$ and a resistor $R_9$, a level setter 56 comprising a variable resistor $VR_2$ and a fixed resistor $R_{11}$, and an integrator circuit 57 comprising an operational amplifier $OP_2$, a diode $D_5$, a capacitor $C_3$ and resistors $R_{12}$, $R_{13}$ and $R_{14}$. An ordinary AGC amplifier has a decrease in the gain as the gain control voltage $V_A$ increases as shown by the curve K. Therefore, unlike FIG. 3, the diode $D_4$ is connected in the reverse polarity direction and level setting is carried out by applying a positive voltage thereto. An analog switch 54 provides a signal level of only the sample position of the sample gate signal. When the switch is set to terminal 1 (sample position), feedback is effected to the AGC amplifier 52, both inputs of the operational amplifier $OP_2$ are grounded on the side of the terminal 2 and the gain of the amplifier 52 is fixed. The level setting is also performed through the analog switch in order to prevent any change in the output level due to the sample gate width. In this case, the AGC amplifier 52 is inserted at an intermediate position because, (1) it is difficult to use this amplifier at the initial stage due to a high noise level, and (2) the maximum amplitude changes since a DC bias changes. In order to make the maximum amplitude constant, the amplifier 53 is inserted in a successive stage of the receiving amplifier 5.

Figure 6:
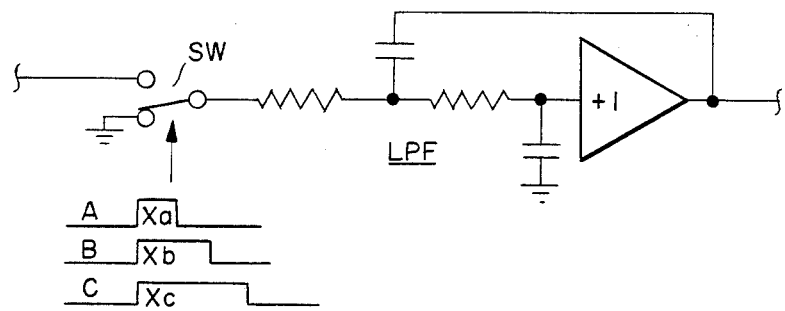
FIG. 6 is a schematic diagram of a gate circuit of a Doppler detector.
Figure 7:
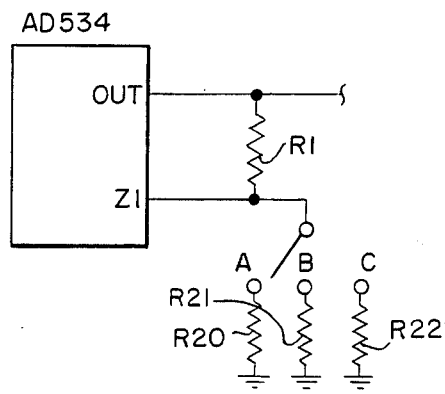
FIG. 7 is a diagram of an amplification degree selecting circuit of a multiplier used in the amplitude equalizing circuit.

This invention is also effective in a case where the gate circuit shown in FIG. 6 is used in place of the sample and hold circuits 63 and 73 of the Doppler detectors 6 and 7. This gate circuit equivalently comprises the switch SW and the low-pass filter LPF and changes a sample volume by changing the widths ta, tb, . . . of the gate signals A,B, . . . of the switch. When the gate width is changed as described above, the output amplitude changes, but the change is absorbed by the amplitude equalizing circuit 20 shown in FIG. 2. At this time, if the gain of the integrated circuit chip AD 534 used in the multipliers 21 and 22 is changed by the gate signals A, B and C as shown in FIG. 7, the maximum amplification degree also changes and a more effective result can be obtained. The resistors $R_{20}$ and $R_{22}$ correspond to the resistor $R_2$ of FIG. 3 and the following relationship exists:

$$R_{20} < R_{21} < R_{22}$$

In this case, the following relation is obtained between the gate widths ta, tb, . . . and the gain:

$$ta[(R_1+R_{20})/R_{20}] \leq tb[(R_1+R_{21})/R_{21}] \leq tc[(R_1+R_{22})/R_{22}]$$

As described above, according to the invention, manual gain adjustment and cut-off frequency adjustment are no longer necessary, thereby improving the operability of the device. In addition, an input amplitude of the Doppler analyzer is always sufficient and the accuracy of the system is improved. The invention permits manual selection of the cut-off frequency of the high-pass filter. Moreover, since the automatic adjusting range is about fc/2, the changeable range of fc can be widened in combination with the manual adjustment.

I claim:

1. An ultrasonic pulse Doppler blood flow meter operatively connected to transmit and receive ultrasonic wave signals, having a specific repetition frequency, to and from living body tissue, comprising:
   an ultrasonic probe for transmitting the ultrasonic wave signals to the living body tissue and receiving the ultrasonic wave signals from the living body tissue at the specified repetition frequency;
   a receiving amplifier, operatively connected to said ultrasonic probe, for amplifying the received ultrasonic wave signals from the ultrasonic probe and outputting an output signal;
   a Doppler detector, operatively connected to said receiving amplifier, for mixing the output signal of said receiving amplifier with a reference signal and for generating a Doppler signal of a specified depth having a low frequency element;
   a high pass filter, operatively connected to said Doppler detector, for eliminating the low frequency element of the Doppler signal and outputting a high pass filtered signal;
   an amplitude equalizing circuit, operatively connected to said high pass filter, for substantially equalizing the amplitude of the high pass filtered signal to a predetermined signal level and outputting an equalized signal;
   a Doppler analyzer, operatively connected to said amplitude equalizing circuit, for analyzing the equalized signal of said amplitude equalizing circuit; and
   a display, operatively connected to said Doppler analyzer, for displaying the result of the analysis of said Doppler analyzer.

2. An ultrasonic pulse Doppler blood flow meter according to claim 1, wherein said receiving amplifier comprises an automatic gain control receiving amplifier for maintaining a substantially constant amplitude of the received ultrasonic waves from the specified depth.

3. An ultrasonic pulse Doppler blood flow meter according to claim 1, wherein said amplitude equalizing circuit comprises:
   a multiplier operatively connected to said high pass filter;
   an integrator circuit operatively connected to said multiplier;
   a rectifier, operatively connected between said multiplier and said integrator circuit, for detecting the amplitude of the output of said high pass filter; and
   a level setter, operatively connected to said integrator circuit, for designating a desired signal level.

4. An ultrasonic pulse Doppler blood flow meter according to claim 1, wherein said Doppler detector comprises:
   a gate circuit, operatively connected to said receiving amplifier for receiving the output signal and outputting a gate signal, comprising:
      a switch operatively connected to receive the gate signal; and
      a low pass filter operatively connected to said switch.

5. An ultrasonic pulse Doppler blood flow meter according to claim 1, wherein said receiving amplifier comprises:
   a preamplifier, operatively connected to said ultrasonic probe, for receiving the ultrasonic signals;
   amplifiers operatively connected to said preamplifier;
   a half-wave rectifier operatively connected to said amplifiers;
   a level setter circuit operatively connected to said half-wave rectifier;
   an analog switch circuit operatively connected to said level setter circuit; and
   an integrator circuit operatively connected to said analog switch circuit and said amplifiers.

6. An ultrasonic pulse Doppler blood flow meter according to claim 1, wherein said Doppler detector comprises an orthogonal detector for providing real and imaginary components of the Doppler signal;
   wherein said high pass filter comprises first and second high pass filters operatively connected to receive the real and imaginary Doppler signals, respectively; and
   wherein said amplitude equalizing circuit provides gain control at the same rate for both the real and imaginary components of the Doppler signal, only one amplitude component of the real and imaginary Doppler signals being detected and equalized.

7. An ultrasonic pulse Doppler blood flow meter according to claim 1, wherein said Doppler detector comprises an orthogonal detector, for detecting real and imaginary components of the Doppler signal;

wherein said high pass filter comprises first and second high pass filters operatively connected to receive the real and imaginary components of the Doppler signal, respectively; and wherein said amplitude equalizing circuit equalizes the amplitude of both the real and imaginary components of the Doppler signal at the same rate, by detecting both components and maintaining the relationship $R^2+I^2=K$, where R is the real component, I is the imaginary component and K is a constant.

8. An ultrasonic pulse Doppler blood flow meter including an ultrasonic probe for transmitting ultrasonic wave signals to living body tissue and receiving the ultrasonic wave signals from the living body tissue at a specific repetition frequency, and a Doppler detector circuit, operatively connected to the ultrasonic probe, for mixing the ultrasonic wave signals with a reference signal and generating a Doppler signal, said ultrasonic pulse Doppler blood flow meter further comprising:

an amplitude equalizing circuit, operatively connected to the Doppler detector circuit, for substantially equalizing the amplitude of the Doppler signal to a predetermined signal level and outputting an equalized signal, said amplitude equalizing circuit comprising:

a multiplier circuit operatively connected to the Doppler detector circuit;

an integrator circuit operatively connected to said multiplier circuit;

a rectifier circuit, operatively connected between said integrator circuit and said first multiplier circuit, for detecting the amplitude of the Doppler signal; and a level setter circuit, operatively connected to said integrator circuit, for designating a desired signal level.

* * * * *

UNITED STATES PATENT AND TRADEMARK OFFICE
CERTIFICATE OF CORRECTION

PATENT NO. : 4,541,437

DATED : SEPTEMBER 17, 1985

INVENTOR(S) : SHIN-ICHI AMEMIYA

It is certified that error appears in the above-identified patent and that said Letters Patent is hereby corrected as shown below:

FRONT PAGE [56] References Cited
   line 5, "4,357,278" should be --4,257,278--; and
          "Papadofrongakis et al." should be
          --Papadofrangakis et al.--.

Col. 2, line 57, " A - A" should be --Ⓐ-Ⓐ--.

Col. 3, line 2, "$\sqrt{R^2+I^2}$" should be -- $\sqrt{R^2+I^2}$--;

line 40, "A - A" should be --Ⓐ-Ⓐ--.

Signed and Sealed this

Eleventh Day of February 1986

[SEAL]

Attest:

DONALD J. QUIGG

Attesting Officer

Commissioner of Patents and Trademarks